United States Patent [19]

Bey, Jr. et al.

[11] Patent Number: 5,461,322

[45] Date of Patent: * Oct. 24, 1995

[54] AUTONULLING DC BRIDGE FOR REAL-TIME SENSOR TRANSDUCTION AND VOLTAGE MEASUREMENTS

[75] Inventors: Paul P. Bey, Jr., Temple Hills, Md.; Thomas L. Fare, Glenside, Pa.; David J. Yonce, Alexandria, Va.

[73] Assignees: Geo-Centers, Inc., Rockville, Md.; Naval Research Laboratory, Washington, D.C.

[*] Notice: The portion of the term of this patent subsequent to Nov. 23, 2010 has been disclaimed.

[21] Appl. No.: 102,835

[22] Filed: Aug. 6, 1993

Related U.S. Application Data

[63] Continuation-in-part of Ser. No. 783,904, Oct. 29, 1991, Pat. No. 5,264,798.

[51] Int. Cl.[6] ................................... G01R 17/02
[52] U.S. Cl. ................ 324/706; 324/725; 324/98; 323/365
[58] Field of Search .................... 324/705, 706, 324/725, 98, 99 R; 323/365, 366, 367

[56] References Cited

U.S. PATENT DOCUMENTS

| | | | |
|---|---|---|---|
| 4,015,209 | 3/1977 | Meyer-Ebrecht | 324/99 R X |
| 4,795,965 | 1/1989 | Dooley | 324/98 X |
| 5,159,277 | 10/1992 | Mount | 324/706 X |
| 5,189,362 | 2/1993 | Doble | 324/706 X |
| 5,264,798 | 11/1993 | Bey et al. | 324/725 |
| 5,309,085 | 5/1994 | Sohn | 324/705 X |

*Primary Examiner*—Kenneth A. Wieder
*Assistant Examiner*—Glenn W. Brown
*Attorney, Agent, or Firm*—Oblon, Spivak, McClelland, Maier, & Neustadt

[57] ABSTRACT

A feedback operated DC bridge circuit for monitoring the voltage variations in a voltage divider circuit using a voltage controlled resistance component to reach a null balance across the bridge. Amplification is provided at higher accuracy near the null point when the voltage difference across the bridge is zero. The feedback bridge circuit includes an integrator which directly drives the controlling component to the value of the resistance in an unknown branch to force the null condition. The voltage controlled component (configured as a discrete metal oxide semiconductor device or bipolar junction transistor) and the balancing scheme are suitable for microfabrication and provides noise-rejection enhancement. The interconnected integral feedback of the autonulling DC bridge enables both a neural network for pre-processing sensor input in a spatial domain as well as general analog computation that mimics a first order differential equation in the form of the system state equation.

8 Claims, 7 Drawing Sheets

AUTONULLING DC BRIDGE FOR REAL-TIME SENSOR TRANSDUCTION AND VOLTAGE MEASUREMENTS

This application is a continuation-in-part of application Ser. No. 07/783,904 filed on Oct. 29, 1991 now U.S. Pat. No. 5,264,798.

BACKGROUND OF THE INVENTION

1. Field of the Invention

The present invention relates to a feedback operated DC bridge for monitoring voltage variations in a voltage divider circuit used with a voltage controlled resistance component to reach a null balance across the bridge.

2. Discussion of the Background

Figure 1:
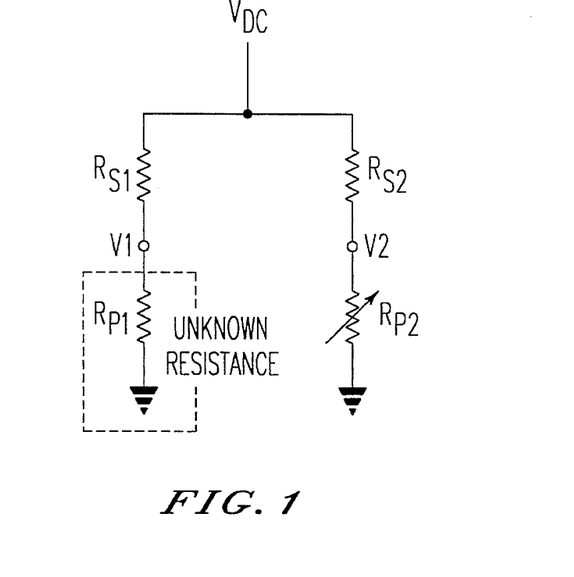
FIG. 1 is a prior art standard DC bridge or Wheatstone bridge configuration.

In order to provide sensor measurements such as temperature, pressure and chemical detection, there is a need for determination of the accurate equivalent resistance of a sensor in response to changes in the environment. Some systems can be modeled as a resistor with the value of the resistor determining the state of the system such as the resistance in a temperature sensor, the piezo-resistance in pressure sensors, or the conductance in a chemical sensor. Thus it is critical to have a resistance transducer that can maintain a stable reading regardless of any noise in the system. Voltage dividers or bridge networks can be used to provide accurate measurements when these systems use resistance sensitive devices. Prior art systems use either a voltage divider approach to determine the value of the unknown resistance or bridge configurations which make use of the off-null signal, V1–V2, to correlate the measurement of an unknown signal transducer 10 as shown in FIG. 1.

Previous bridge measurements require that the off-null signal be equated with the unknown resistance by relationship with the difference voltage or, if the bridge was to be nulled, manual adjustments were required to yield values of the unknown resistance corresponding to settings on a potentiometer that in some cases take several seconds to null.

The prior art systems are sufficient only when the off-null signal remains within a given range and they can be directly correlated with the unknown environmental condition which is being transduced or they are effective when the systems only require a knowledge of whether a signal is above or below a predetermined point. However, when the deviation of the unknown node voltage, V1, is distant from the set point, V2, large gain cannot be used for the off-null signal therefore requiring that the set-point be adjusted or the gain be reduced. Applicants have developed a bridge measurement which addresses this prior art problem.

SUMMARY OF THE INVENTION

Accordingly, one object of the present invention is to provide a feedback bridge circuit whereby the difference voltage across a bridge reaches a point of stability when it is zero to thereby provide for amplification with higher accuracy near the null point.

It is another object of the present invention to provide a feedback bridge circuit wherein the output of the integrator directly drives the controlling component to the value of the resistance in an unknown branch thereby forcing a null condition across the bridge.

It is a further object of the invention to provide a feedback bridge circuit wherein the voltage-controlled component in the balancing scheme is a discrete metal oxide semiconductor (MOS) device or bipolar junction transistor suitable for a microfabrication and providing noise-rejection enhancement.

It is a further object of the present invention to provide a feedback control circuit wherein the nonlinearity of the voltage divider scheme for biasing the feedback branch provides a signal-to-noise ratio improvement for the autonulling bridge feedback system.

It is a further object of the present invention to provide a feedback bridge circuit having integral feedback wherein the system serves as a band pass filter for input signals whose frequency response can be adjusted by changing the integrator time constant.

It is a further object of the present invention to utilize the autonulling DC bridge as a single transduction cell in a nearest-neighbor interconnected neural network.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 2:
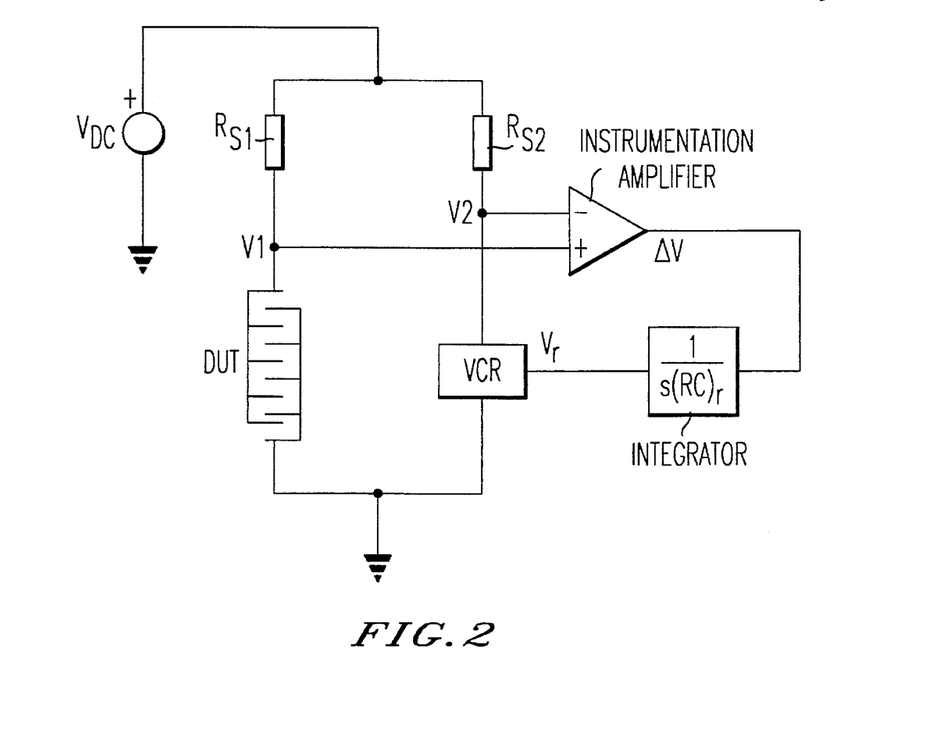
FIG. 2 is a block diagram of an autonulling DC bridge according to the present invention.

Referring now to the drawings, wherein like reference numerals designate identical or corresponding parts throughout the several views, and more particularly to FIG. 2 thereof, there is shown a design for an improved bridge measurement in an autonulling DC bridge suitable for incorporation to resistance sensitive devices or transient voltage transducers. The self-contained device of the present invention requires only a digital voltmeter to measure the output voltage, $V_r$. The voltage-controlled resistance (VCR) of FIG. 2 corresponds to $R_{p2}$ in FIG. 1 and the device under test of FIG. 2 corresponds to $R_{p1}$. The system reaches a stable measurement corresponding to variations in the resistance $R_{p1}$ or the input voltage V1 in less than a millisecond for particular system parameters. Output voltages are calibrated to outputs for known resistances or input voltages and can be used to transduce signals from pressure, temperature or chemical sensors. A DC voltage is applied across the bridge and the current divides into the branches according to the resistance of each branch. For a value wherein $R_{s1}=R_{s2}$, the difference in voltage V1–V2 across the bridge is zero if and only if the resistances $R_{p1}$ and $R_{p2}$ are equal or the equivalent resistance of the device under test is equal to the voltage control resistance which operates monotonically.

Figure 3:
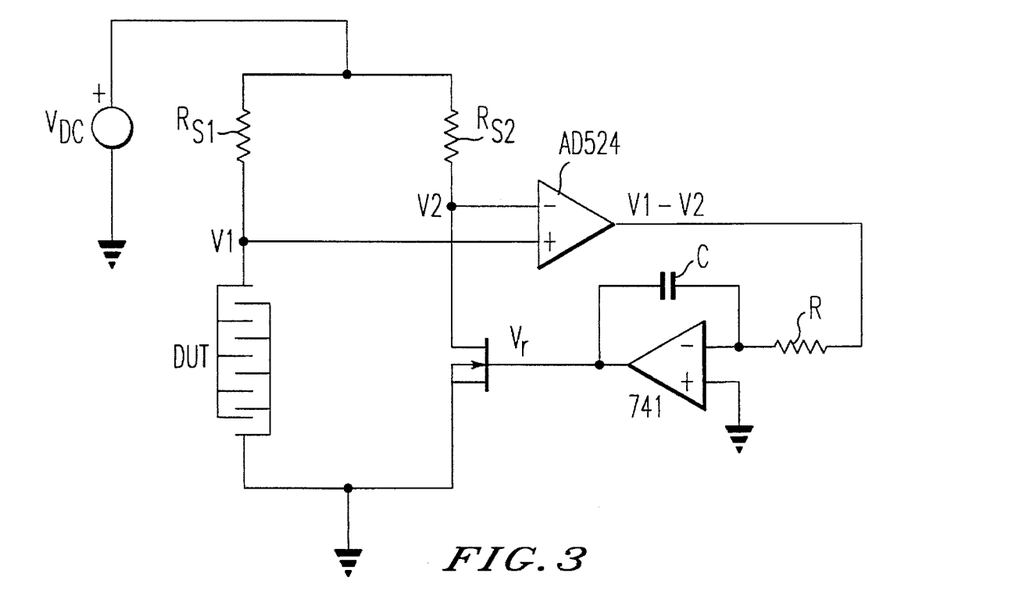
FIG. 3 is a schematic diagram of the autonulling DC bridge of FIG. 1.

The nulling circuit of the bridge is an analog feedback network which establishes a stable null across the bridge for a wide range of resistor values with a minimum of supporting hardware. FIG. 3 shows a schematic realization of a particular circuit with a MOSFET as the voltage controlled resistance. The difference voltage across the bridge, V1–V2 is fed into an integrator which in turn drives the gate of the MOSFET. The feedback signal from the integrator varies until the difference across the bridge is zero. At that time, the feedback loop is at a stable point because the difference signal is zero and the integrator output remains constant. The stability of the feedback network meets standard stability criteria when theoretically analyzed.

The autonulling DC bridge circuit of the present invention is especially suitable for microfabrication because all of the elements of the feedback system can be integrated into silicon and are thus readily compatible with silicon-based electrode sensors and micromachined silicon devices. Utilizing this approach provides high noise rejection due to the differential measurement taken across the bridge nodes. Any noise which is local to the integrated silicon device can be subtracted because this kind of interference is common to the nodes in close proximity to each other on the micron scale. The system also provides an output voltage directly proportional to the unknown resistance due to the transfer characteristics of the feedback element, VCR, rather than the measured signal dependence derived from the voltage divider or bridge off-null relationships. The system is also usable for following transient voltage signals in a generalized bridge configuration in which V2 is driven so that it follows V1 by the autonulling feedback system.

The ability to fabricate a bridge in silicon facilitates the measurements of resistances of many systems which are prone to noise pick-up (e.g., photodiodes and small current amplifiers).

Some of the noise contributors are minute perturbations in the surroundings which cause dramatic changes to the system's steady state because of the small active areas and the high gain which is required in such systems. The silicon fabrication of the devices of the present invention addresses this problem.

Advances in lithographic techniques allow for the patterning of living organisms (the ultimate chemical sensors) and other chemically sensitive systems on surfaces. The bridge designed according to the present invention provides a method for transducing changes in the system's function during a real time format. This enables the fabrication or large arrays of these kinds of bridges which can be sampled individually. Such an array can be used, when each bridge has the same chemical-sensitive systems, in order to increase the reliability of the detection of one component. These arrays can also be used when there are different combinations of chemical-sensitive films in order to enable the detection of mixtures of chemical species with appropriate signal analysis algorithms.

Figure 4:
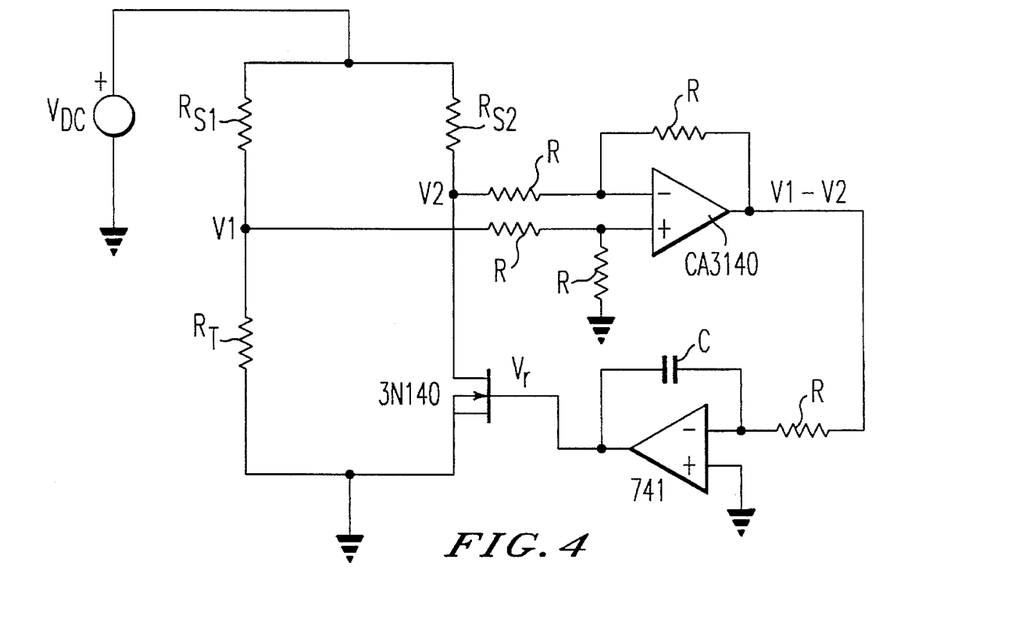
FIG. 4 is a schematic diagram of an autonulling DC bridge having a discrete silicon thermistor as the device under test (DUT)

An example of an autonulling DC bridge configured using discrete elements and with integrated circuits is shown in FIG. 4. $V_{DC}$ is set to +5 volts and the values of RS1 and RS2 were chosen to be equal at 1 kΩ. The resistance in the unknown branch (DUT or $R_{t1}$), is a thermistor with a negative temperature coefficient of '=–2.9%/°C., and the voltage controlled resistance in the control branch is a n-channel metal oxide semiconductor field effect transistor, MOSFET (3N140 or NTE221). This MOSFET is a dual gate device for signal modulation and it is used with gates connected together in order to make its characteristics similar to a conventional signal gate MOSFET. The difference voltage across the bridge, V1–V2 is obtained using an operational amplifier configured as a difference amplifier (CA3140 with R=1kΩ). The voltage is fed into an operational amplifier integrator (741 with R=1kΩ and C=0.1 microfarad). The output of the integrator 741 drives the gate of the MOSFET directly. An oscilloscope monitors the difference voltage across the bridge, which is the output of the CA3140. The voltage is within 1 millivolt of ground when the thermistor is ambient temperature. When the temperature of the thermistor is forced to a new temperature, the difference voltage changes only very slightly and then resets itself to the same range near ground on the integrator input. This transient change became more apparent for extreme changes in temperature such as would occur when a soldering iron tip is brought close to the thermistor and is then removed. If the temperature reaches a value such that the thermistor's equivalent resistance cannot be reached by that of the MOSFET, then a constant difference voltage remains and the integrator is pinned to the rail voltage. In this example, the stability and the wide range operation of the system is demonstrated along with the correlation of the feedback voltage to the input temperature therefore providing a basis for calibration.

Figure 5:
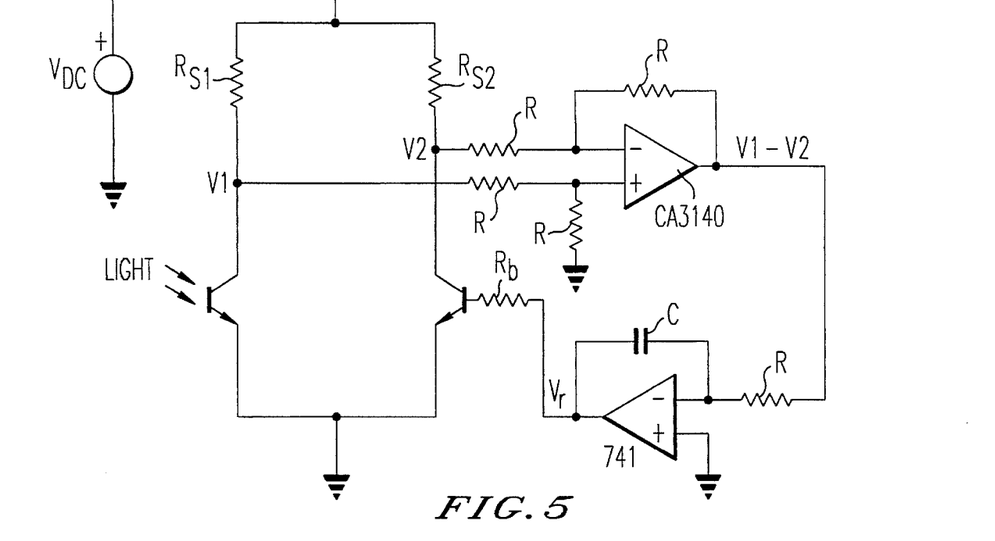
FIG. 5 is a schematic diagram of the autonulling DC bridge according to the present invention having a phototransistor as the device under test for optical transduction and a bipolar junction transistor as the voltage controlled resistance.

In another configuration, as shown in FIG. 5, the dc bridge circuit was modified by replacing the thermistor by a phototransistor (NTE3031) and the MOSFET by a bipolar junction transistor (2N2222) with a current controlling resistance in the base circuit, $R_b$(10 kΩ). The changes which occur in the light level on the phototransistor are followed by changes in the voltage applied to the base circuit of the bipolar junction transistor. A null is measured at the CA3140 output which is at the same level in the circuit of FIG. 4 for a constant light level. A square pulse is applied to a light emitting diode (LED) and directed at the phototransistor with the bridge output voltage, $V_r$, following the square wave and decreasing in magnitude as the LED is moved away.

Figure 6:
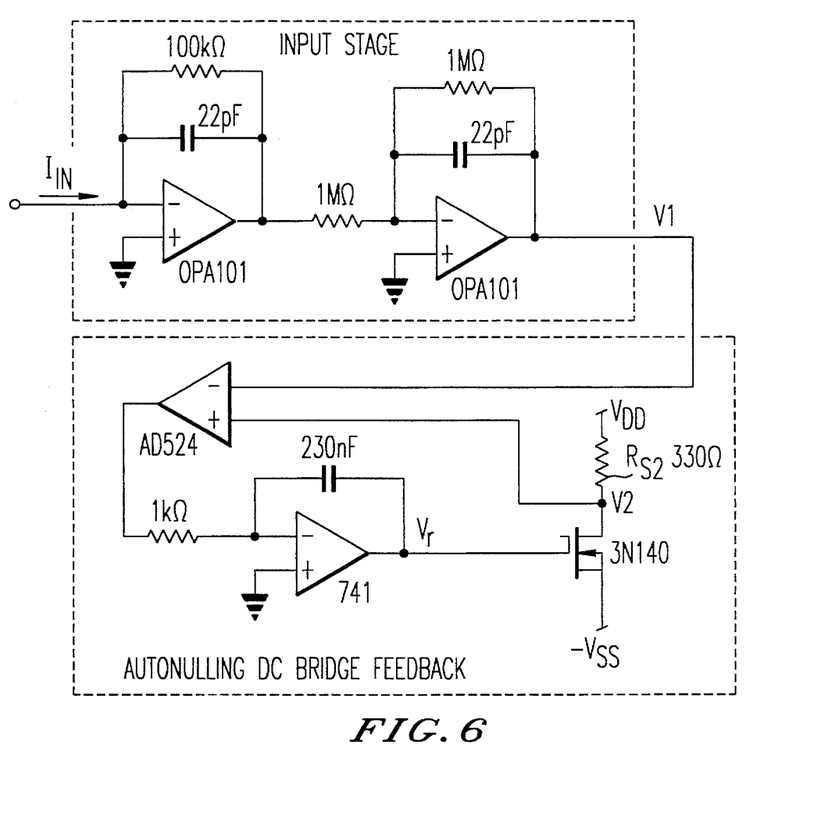
FIG. 6 is a schematic of an autonulling DC bridge embodiment using a current-to-voltage amplifier followed by unity-gain voltage amplifiers as the input stage.

In another embodiment, as shown in FIG. 6, the dc bridge feedback is modified to accommodate variations in V1 around ground or any other reference voltage. FIG. 6 was designed to follow an input voltage, V1, generated by the transduction of a current as opposed to monitoring a resistance through a parallel voltage divider as in the examples of FIGS. 4 and 5. In order for the feedback branch node voltage, V2, to be able to follow the input voltage to negative values, the voltage divider of the feedback branch was biased by $V_{dd}$ and, $-V_{ss}$. These two voltages $V_{dd}$ and $-V_{ss}$ were generated using voltage dividers between 15V and ground and −15V and ground respectively. A 10 kΩresistor was connected to the +15 volts and in series with a 1 kΩresistor which was connected to ground. The node connecting these two resistors generated the voltage $V_{dd}$. A 10 kΩresistor was connected to −15V and in series with a 1 kΩresistor which was also connected to ground with the node between these two resistors providing $-V_{ss}$. The resistance $R_{s2}$ of the feedback branch is set at 330 ohm which was near the middle of the operating range of the MOSFET 3N140 to thereby allow the feedback node voltage to easily operate in the center of the biasing range which is ground in the specific instance discussed above. Biasing voltages were chosen for two particular reasons: a) to provide a finer control to the feedback element when V2 was to be controlled near ground and, b) to control the current magnitude which flows through the feedback branch. Both of these objectives are fulfilled by reducing the voltage across $R_{s2}$ and the MOSFET. These voltages could also be applied by a variation of the above voltage divider scheme with the supplies being adjusted and the center point biased so that the nullable voltage range, the range of V1's variations, can be adjusted as needed. The input voltage V1 is generated by current-to-voltage (I-V) converter and a voltage amplifier set to unity gain. Both stages are constructed using operational amplifiers (OPA101) and precision ¼ watt resistors. The difference voltage is generated by an instrumentation amplifier (AD524) with its gain set to 20. The difference voltage is applied to an operational amplifier (741) configured as an integrator whose output is the feedback voltage ($V_r$), and which drives the MOSFET. The circuit exists in the box labeled "Autonulling DC Bridge Feedback" in FIG. 6.

The configuration of FIG. 6 was tested in an electrochemical system which transduces the charging and discharging current of a polarizable electrode. The square wave which varied between 0 and $V_{max}$ was applied to a petri dish containing biological recording solution by platinum (Pt) electrode with a second Pt electrode being connected to the input stage of the bridge at $I_{in}$. $V_{max}$ was varied over a wide range of values and when it was set at 10 millivolts, the resulting current was approximately 0.1 microamperes. There was a signal-to-noise ratio (SNR) improvement of approximately 20 dB over conventional structure. This high common mode rejection and SNR improvement is due to the differential measurement, integral feedback and the non-linearity of the interaction between the feedback branch and the voltage dividers which generate $V_{dd}$ and $-V_{ss}$.

Figure 7:
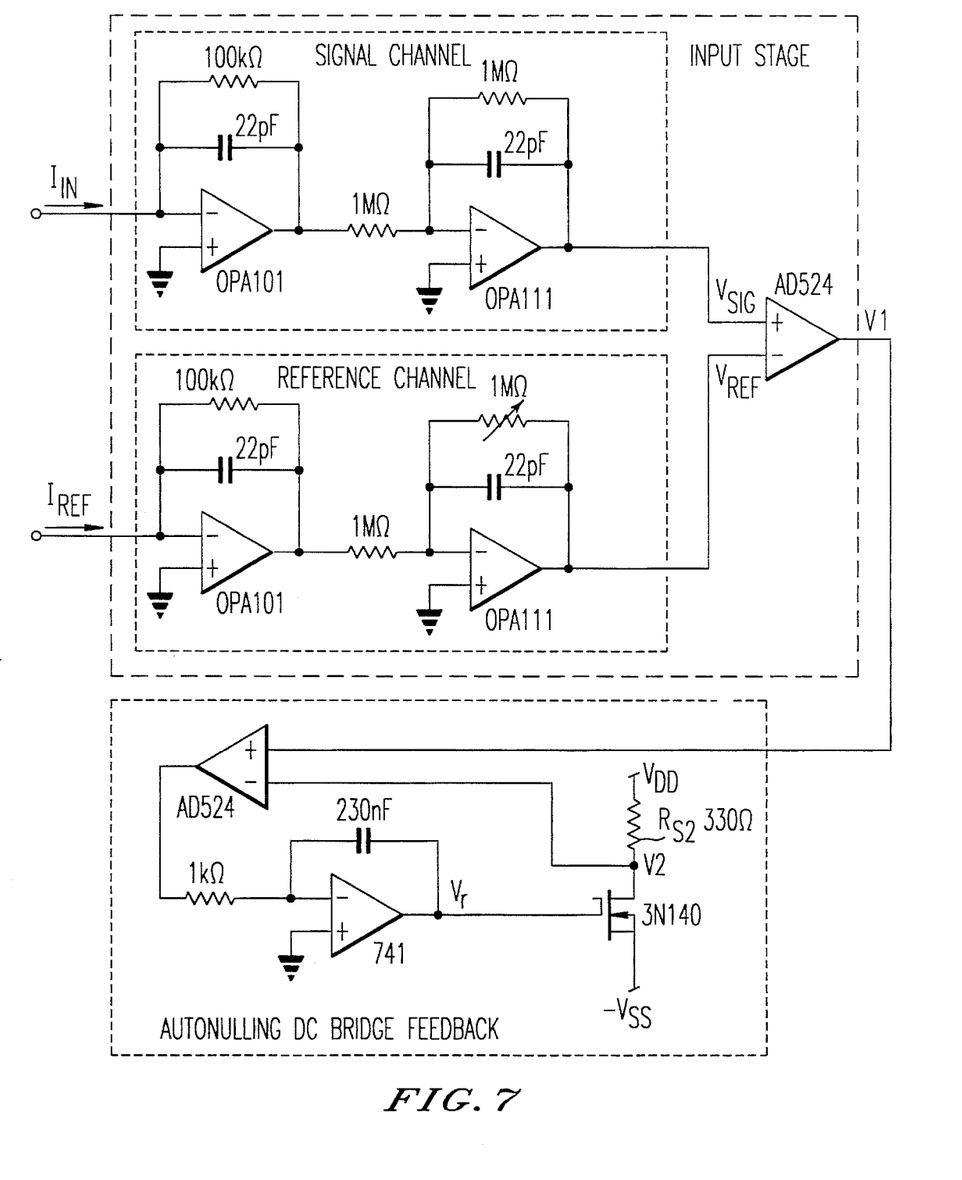
FIG. 7 is an embodiment of the DC autonulling bridge having two high gain current-to-voltage amplifiers forming an input stage.

The ability to handle very high-gain on the input current is brought about by the embodiment of FIG. 7 which uses an addition of a second input stage equivalent to the input stage of FIG. 6 as a reference channel. The output from the reference channel is subtracted from the output of the original input stage using a second instrumentation amplifier (AD524) in order to reduce common electromagnetic (EM) pickup which is a problem occurring in very high-gain I-V converters. The gain on the I-V converters was increased over the gain used in the embodiment of FIG. 6. The voltage amplifier in the reference channel has a variable resistance in order to accommodate slight gain difference to the EM signals of the two parallel channels. In the configuration of FIG. 7, the I-V converters are OTA101s and the voltage amplifiers are OTA111s. The section entitled "Autonulling DC Bridge Feedback" is identical to FIG. 6. The input current to the reference channel, $I_{ref}$, is provided using an identical electrode connection to that of the signal input. This channel is connected to a second petri dish in close proximity to the dish to which the signal was applied. With this configuration the current is able to be reduced by a factor of 100 from that of the current in the configuration in FIG. 6 while the same SNR (signal-to-noise) improvement was obtained. The currents used in the embodiments of FIG. 7 to closely approximate the levels detected in biological systems for which transient current or voltage monitoring is very important.

Figure 8:
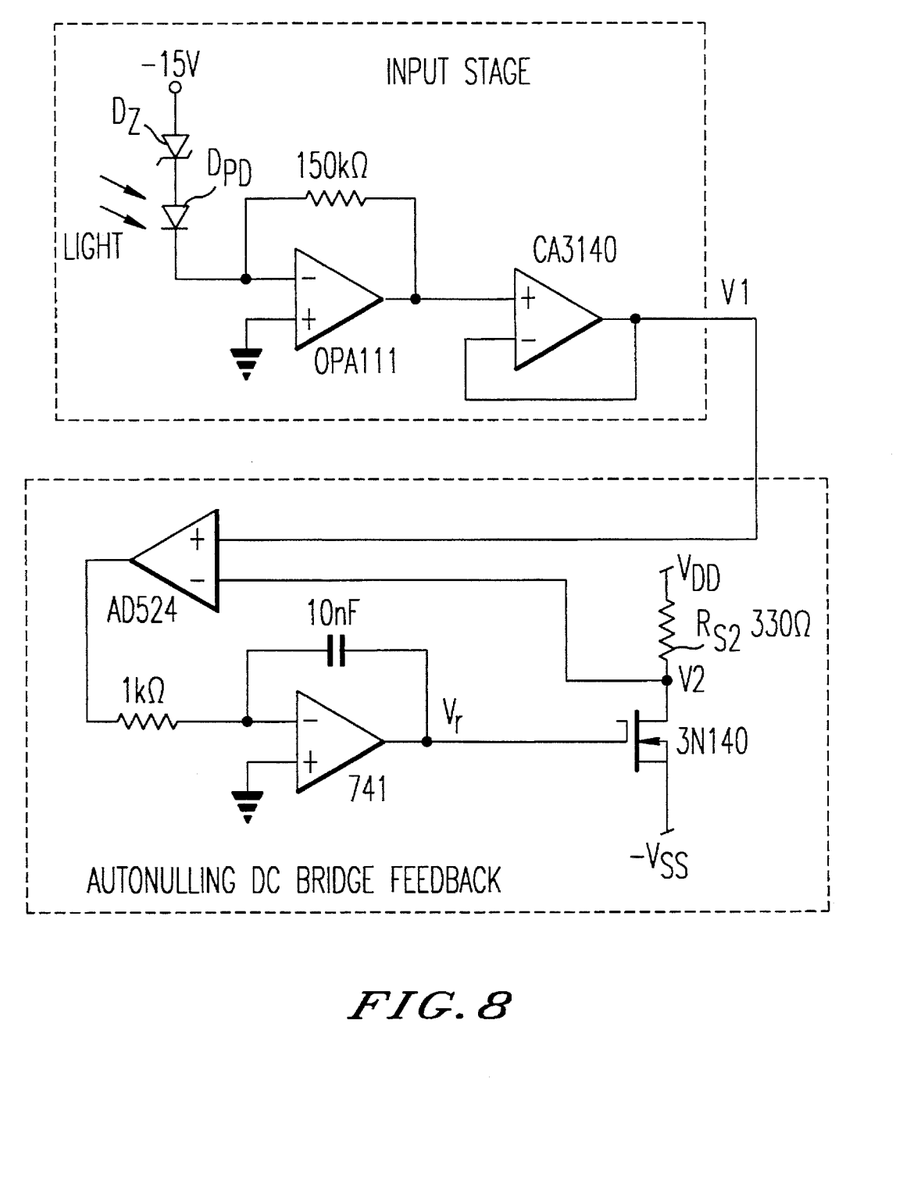
FIG. 8 is an embodiment of the autonulling DC bridge configured with a photodiode for transduction of an optical signal.

The modification provided by the embodiment of FIG. 8 utilizes a photodiode circuit as the unknown transient voltage with the photodiode being run in the photoconductive mode. The photodiode generated V1 which was followed by the same autonulling DC bridge feedback which is the same as FIG. 6. A chopping circuit modulates the LED signal in order to test the ability of the feedback system to follow the input light signal. The configuration of FIG. 8 is sensitive to all impinging light and for tests similar to those used with the embodiment of FIG. 5.

Figure 9:
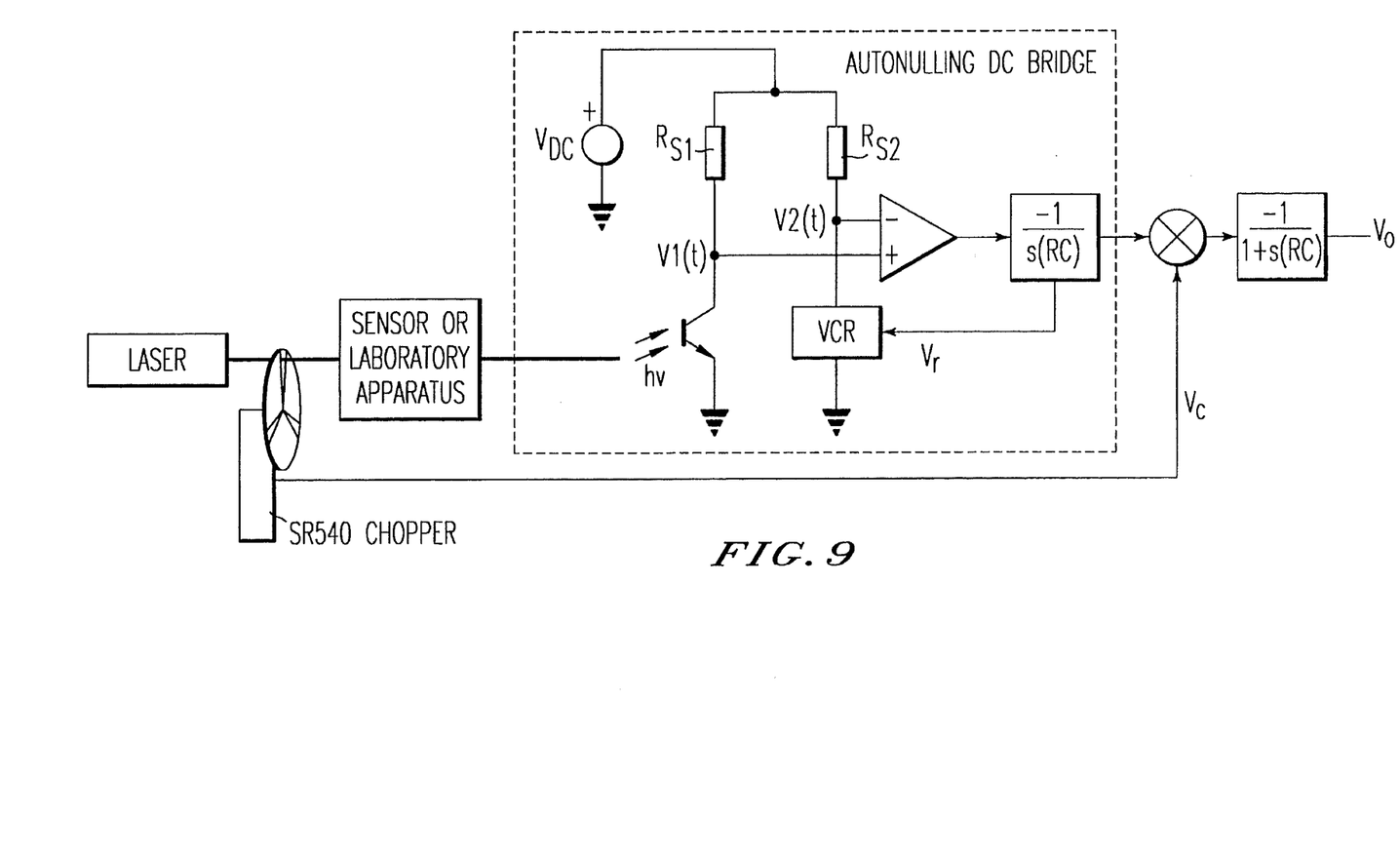
FIG. 9 is a block diagram with a phase-sensitive autonulling DC bridge configured as a transducer element in a modified lock-in-amplifier for optical fiber signal transduction.

The embodiment of FIG. 9 provides another autonulling DC bridge with a phototransistor circuit as the unknown transient voltage but with a chopper on the input light signal and a multiplier on the output voltage in order to extract the frequency component of the excitation. This circuit is configured to transduce a dc signal which corresponds to impinging light being modulated at a constant frequency. The particular circuit is the same as that of FIG. 8 with an additional phase-sensitive detection scheme being added to the output. The light signal is chopped at a fixed frequency by a mechanical chopper SR540. The chopper generates a square wave output voltage, $V_c$, at the frequency of the chopper. An analog multiplier AD 534 is used to take the product of the output voltage, $V_r$, and the chopper voltage, $V_c$. A standard phase-sensitive technique is carried out using a low-pass filter with a cut-off frequency so that the time varying terms obtained from the product are removed. The output of the low-pass filter, $V_o$, is proportional to the product of the magnitudes of $V_c$ and $V_r$ and is related to the phase between $V_r$ and $V_c$. The magnitude of $V_c$ and the phase are both constant when the frequencies are fixed so that the output voltage, $V_o$, varies with the value of $V_r$. $V_o$ varies as the LED is moved both away and towards the detector. The phase-sensitive output is tested by allowing a second LED being modulated at 60Hz to impinge on the detector with the frequency of the chopper being approximately 2 kHz. The interference caused very little change in $V_o$, while significant changes were seen when the first LED focused through the chopper was moved in and out.

Figure 10:
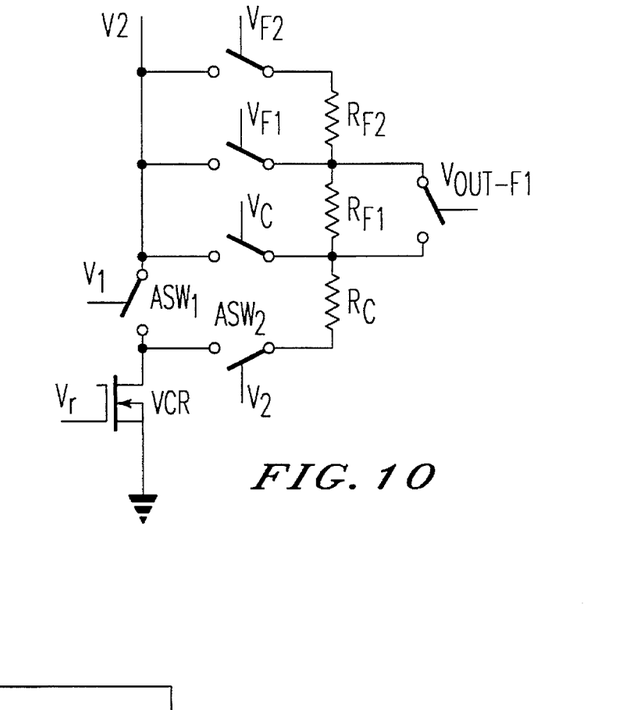
FIG. 10 is a bank switching network scheme for a wide-range voltage-control resistance nulling.

In order to enhance the range of operation, the autonulling DC bridge, switched fixed transistors can be connected in series with the voltage controlled resistance (MOSFET) which provides a wide range of operation as detailed in FIG. 10. The top node of the VCR is connected to two analog switches $ASW_1$ and $ASW_2$. The other side of $ASW_1$ is connected directly to $V_2$ while the other side of $ASW_2$ is connected to a series of resistances and other switches. The control signals for $ASW_1$ and $ASW_2$ are such that only one of the two switches is on at any one time. $ASW_1$ will be "on" when $V_1$ is high while $ASW_2$ will be "off" when $V_2$ is low. The VCR is "in" the circuit and the bank switching network is out of the circuit when $ASW_1$ and $ASW_2$ are in such a respective "on" and "off" state. Because the two operate in a complementary fashion, when $V_1$ goes low then automatically $V_2$ must go high and $ASW_1$ "off" and $ASW_2$ goes "on" which represents the state when the VCR is connected to the banked series of resistances. The other side of each of the resistances is connected to $V_2$ through another analog switch. In this configuration, with the banked resistor switched in, $V_1$ is low and $V_2$ is high, if $V_c$ is high, then only the coarse resistance $R_c$, will be in series with the VCR and both $V_{F1}$ and $V_{F2}$ must be set low. To add $R_{F1}$ to the series, $V_{F1}$ is set high and the others, $V_c$ and $V_{F2}$, must be set low. $R_c$ and $R_{F1}$ would be in series with the VCR (MOSFET). In order to add $R_{F2}$ to the series, $V_{F2}$ is set high and the other $V_c$ and $V_{F1}$ must be set low. On the other hand, if the analog switch is connected in parallel with any resistance, then this resistance will be removed from the network. This is demonstrated by the FIG. 10 wherein the FET is in parallel with $R_{F1}$ and if $V_{F2}$ and $V_{out-F1}$ are high, then $R_c$ and $R_{F2}$ will be in series with the VCR and $R_{F1}$ will be shorted out of the circuit. Every resistor in the bank switching network may have a parallel FET to switch it in and out of the series connection. The combination of these two methods of banked switching resistors in the control branch yields a versatile method of coarse and fine adjustment practical in a nulling algorithm.

Figure 11:
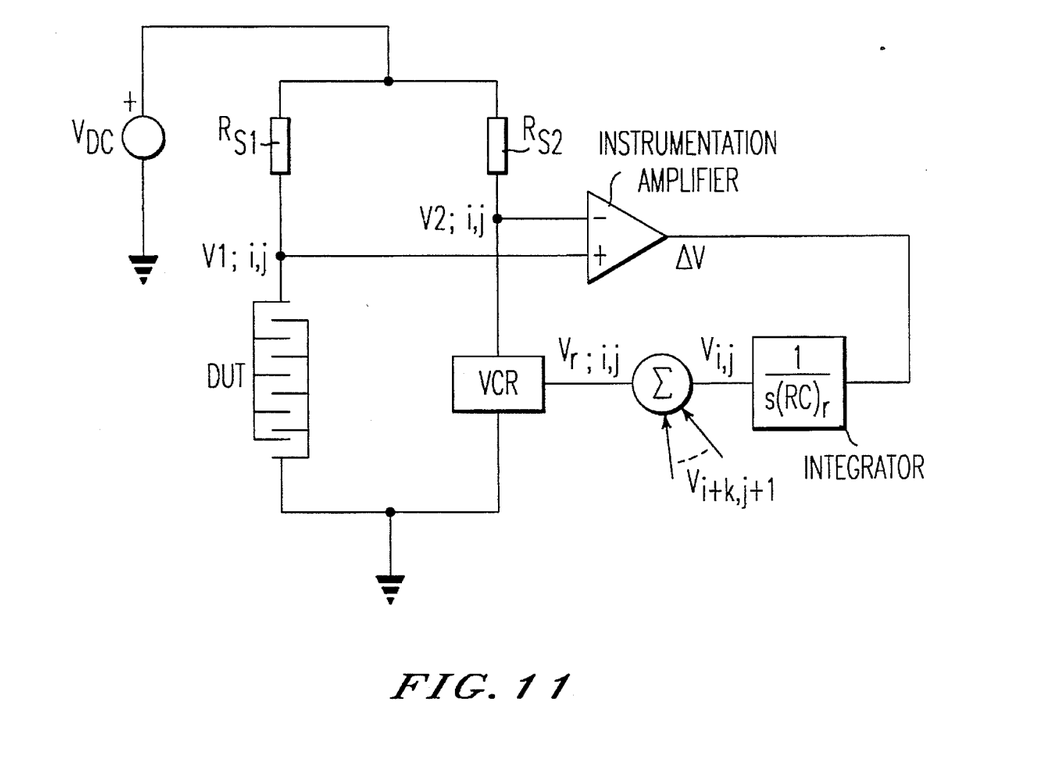
FIG. 11, shows the autonulling DC bridge as the basic structure of a nearest-neighbor interconnected neural network.

In order to take advantage of the autonulling DC bridge in a network environment, the FIG. 11 illustrates a nearest-neighbor interconnected neural network utilizing an autonulling DC bridge as the unit transduction cell. The implementation of FIG. 11 is an optical cellular neural network (OCNN) with each bridge cell being as in the illustrated configuration of FIG. 11 but with the device under test (DUT) being a phototransistor and the voltage controlled resistance (VCR) being a bipolar transistor of the type in FIG. 5. Another variation on this particular embodiment can use a photodiode array as the input scheme with each of the bridges configured as in the FIG. 8, but with the summing device as shown in the FIG. 11 in the loop generating $V_r$ from the neighbors and from itself. Each of the bridge integrators will have outputs that are governed by the coupled differential equation as follows:

$$\frac{dV_{i,j}}{dt} = A(V_{1;i,j} - V_{2;i,j}(V_{r;i,j}))$$

where the state voltage $V_{i,j}$ are the output voltages from each of the bridge integrators and correspond to the system output and $V_{1;i,j}$ and $V_{2;i,j}$ correspond to node voltages of each bridge in the array and i and j correspond to the row and column in the array. $V_{1;i,j}$ corresponds directly to the input signal being transduced at each cell and $V_{2;i,j}$ is the voltage driven by the feedback to follow the input node. Data collected from an array of transducers suffers from spatial noise due to thermal effects on the transducers and local electrical noise at each transduction point. The nearest-neighbor interconnection emulates a cellular neural network that enables spatial convolution or integration over the image as described by Chua and Yang (Cellular Neural Networks: Theory and Applications, IEEE Transactions on Circuits and Systems, 35, pp. 1258–1290 (1988). It allows the weighted interconnection of the feedback signals in the following manner in order to generate the voltage required to balance each bridge in the network, $$V_{r;i,j} = \sum_{k,l=-1}^{1} W_{k,l} \cdot V_{i+k,j+l}$$

where $w_{k,l}$ are the interconnection weights over each of the neighborhoods. The above summation is taken over k and l from −1 to 1 which denotes only nearest-neighbors, but this can be extended indefinitely depending on the shape and corresponding function of the spatial filtration. The weights of the interconnections determine the type of spatial filtering that is carried out by the network and can be positive or negative. Each of the bridges will be at null, so the signal $V_{r;i,j}$ that controls the VCR of each bridge will correspond to the input signal on that bridge, but the signal $V_{i,j}$ will be the signal corresponding to a spatially filtered output from that point in the array.

Conventional techniques for filtering spatial noise was previously done with a computer on data after it is collected and stored using a deconvolution algorithm and a spatial operator. The weighted interconnection of the bridge feedback signals generates a two-dimensional preprocessed image. The technology used in this network is compatible with microfabrication and therefore offers itself to miniatured operation.

The configuration of FIG. 11 has particular application for a two-dimensional optical transduction which can either be mounted under a substrate properly passivated for a cellular or chemical deposition to monitor transmission of light signals through the chemical system or as a focal plane array. Furthermore, such a configuration is effective with signals transduced from substrate-based electrodes or sensors (e.g. temperature or pressure) as an input method in which case a two-dimensional electrical image is transduced.

The system equations for the OCNN are similar to a general formulation developed by Cohen and Grossberg. (The quantized geometry of visual space: The coherent computation of depth, form, and lightness; Behav. and Brain Sci., 6, pp. 625–92 (1983)) for the state equation of locally interconnected shunting inhibitory neural networks. These generalized equations show that the state equations discussed above can also be applied to many other paradigms of neural network (e.g. content addressable memory, short term memory) implying therefore that the interconnected autonulling DC bridge (ADCB) of the present invention readily lends itself to other applications aside from the OCNN. Furthermore, this type of state equation also demonstrates the capability of the system to be applied as an analog processor for spatial signals which are not necessarily transduced using sensors, but used instead for general computation on an analog input array (or vector) with the results of the state equations taken from the system output, $V_{i,j}$ (analog computation). Other schemes, aside from linear weighted sums of the neighboring signals, (e.g. products, derivatives etc.) are also feasible thereby providing a variety of spatial filtering algorithms incorporated into the system.

Aside from the embodiments discussed and particularly exemplified in the FIGS. 2–11, other modifications which do not depart from the scope of the invention may be used to address certain improvements throughout the feedback bridge circuit.

As an example, when $R_{S1}=R_{S2}$, the range of the nulling capability of the voltage control component must be equal to the range of the unknown components. By varying the value of $R_{S1}$ with respect to $R_{S2}$, the range of values of in the various embodiments of the present invention can be nulled by $R_{P2}$ being varied in direct proportion to the ratio $R_{S2}/R_{S1}$. These variations can be obtained by connecting resistances with analog switches in parallel with each resistance being in series to represent either $R_{S1}$ or $R_{S2}$. Their respective values can be changed stepwise by applying appropriate control voltages to the switches. These switches that are "on" represent a short-circuit of the resistor, taking it out of the series connection while the switches that are "off" leave the resistors in the circuit. This provides a digital method for selecting resistance ranges in a stepwise manner, however, as with the actual nulling VCR, the use of an analog gate could be used to vary the values of $R_{S1}$ and $R_{S2}$ continuously while p-channel MOSFET's could be used with the sources connected to $V_{dc}$.

In order to provide for auto-gain amplifier structure for more accurate nulling, an automatic gain control differential amplifier could be used which takes a difference across the bridge in order to enable increasing the gain of the difference signal as its magnitude becomes small. The time constant of the integrators in the feedback can be chosen to cause the difference voltage to vary at time constants similar to those of the unknown variation. Therefore the time constant of the auto gain should be longer in order to enable the feedback to stabilize before either increasing or decreasing the gain. Decreasing the gain will occur immediately if the system drives the integrator to one rail voltage or the other. Even though the system will eventually come to a null, oscillations may occur if the gains remain too high. Implementation results from the use of a comparator and peak detector or averaging circuit in conjunction with an adjustable gain instrumentation amplifier. The gain could be varied at fixed time intervals if and when the peak level of the voltage difference signal has reached a certain level for a given length of time.

Furthermore, increased frequency selectivity could be provided by using a bandpass filter on the difference signal from the bridge which helps to isolate the unknown signal variations.

Utilizing the autonulling DC bridge of the present invention provides significant advantages over prior art configurations and also provides for a suitable application for many types of sensors. Principal among these advantages are that:

the difference voltage across the bridge reaches a point of stability when it is zero; thus, it can be amplified providing higher accuracy near the null point. Differential measurements also yield a high noise rejection because noise is subtracted from both sides of the bridge;

the output of the integrator directly drives the controlling component to the value of the resistance in the unknown branch forcing a null condition across the bridge. The range of operation of the voltage-control discrete component is correlated with the unknown values by a calibration curve that relates the feedback voltage to a resistance value or a voltage V1;

the voltage controlled resistance in the balancing scheme is a discrete metal oxide semiconductor (MOS) device or bipolar junction transistor, making it ideal for micro fabrication. This enables the incorporation of the method with a micron-scale topology. Noise-rejection of the system is enhanced because the differential measurement on the device is subject to the same noise in the environment at this scale;

noise on either V1 or V2 will be attenuated significantly because of the integral feedback. The system serves as a bandpass filter for the input signal wherein the frequency response of the input signal is adjusted by changing the integrator time constant. This system is asymptotically stable leading to the possibility of very high loop gain while maintaining stability and increasing the speed of the response. The loop-gain can be increased by increasing the gain on the differential amplifier state and/or by decreasing the integration time, RC (stray capacitance can lead to ringing if the loop-gain is too high);

the non-linearity of the voltage divider scheme for biasing the feedback branch adds to the signal to noise ratio improvement for the autonulling DC bridge feedback system.

Another potential application for the circuit of the present invention is for its use as voltage matching on a front-end amplifier. With this circuit connected to source and receiver, it is possible to adjust the input resistance of the receiver to match the output resistance of the source. By matching the load to the source, the power transfer from the source to the receiver is maximized. The circuit can be used in a similar manner for automatic gain control applications.

Furthermore, the DC bridge can be used as a voltage following device for transient signal detection which monitors a transient voltage or a voltage generator from a current in order to use the output of a calibrated autonulling DC bridge to compare signals with known signal characteristic in a lookup table. This circuit also has potential for transducing small signals from photosensitive elements and electrodes which are substrate-based and disposable in chemical sensors and laboratory equipment.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured By Letters Patent of the United States:

1. An autonulling bridge circuit system for measuring resistance changes, comprising:

a DC bridge circuit including two current dividing branches with a first branch including a sensor resistance to be measured and a second branch including a voltage controlled resistance means wherein said voltage controlled resistance means is one of a MOSFET and a bipolar junction transistor and wherein each of said first and second branches receives a direct current voltage, said bridge circuit further including a first and second output voltage means each connected to a respective one of said first and second branches;

bridge nulling circuit responsive to output of said first and second voltage output means to provide a difference voltage, said bridge nulling circuit also including an integrator means for providing a feedback signal for driving said voltage controlled resistance wherein said feedback signal varies until the difference between said first and said second voltage output is zero at which point said feedback signal remains constant and is proportional to said sensor resistance as a function of the transfer characteristics of said voltage controlled resistance.

2. The system according to claim 1, wherein said sensor resistance is a phototransistor and wherein said system further includes a phase-sensitive detection apparatus including a light source chopped at a fixed frequency by a mechanical chopper in order to generate a square wave output voltage being fed to one input of an analog multiplier with the second input of said multiplier receiving said feedback signal and with the output of said multiplier being fed to a low pass filter to provide a filter output proportional to the product of said feedback signal and said chopper voltage whereby the magnitude of said chopper voltage and the phase of said chopper voltage are constant when the frequency of said chopper is fixed to thereby provide that said filter output is proportional only to the value of said feedback signal.

3. The system according to claim 1, wherein said sensor resistance is a phototransistor.

4. An autonulling bridge circuit for measuring small transient currents, comprising:

an input stage receiving an input transient current and including a current-to-voltage converter means and a voltage amplifier, said input stage providing an input stage voltage; and autonulling DC bridge feedback means including a means for producing a feedback branch node voltage output for following said input stage voltage wherein said means for producing said feedback branch node output voltage includes a voltage divider means having two biasing DC voltages, a voltage controlled resistance and resistance means having a value substantially centered about an operating range of said voltage controlled resistance means, wherein said bridge feedback means further includes a difference amplifier means for receiving said input voltage and said feedback branch node voltage and providing a difference voltage output to an integrator means wherein said integrator means controls said voltage control resistor in response to said difference voltage.

5. The system according to claim 4, wherein said difference amplifier is an instrumentation amplifier and said voltage controlled resistor is a MOSFET.

6. The system according to claim 4, wherein said input stage further includes a reference current-to-voltage converter receiving a reference current and providing an output reference voltage and wherein said output reference voltage is fed to an input stage amplifier in order to subtract common background electromagnetic pickup for high gain amplification.

7. The system according to claim 4, wherein said input current is generated by a photodiode.

8. A nearest-neighbor interconnected neural network for measuring resistance changes, comprising:

an array of rows and columns of transduction cells with each transduction cell including a DC bridge circuit having two current dividing branches with a first branch including a sensor resistance or transient voltage to be monitored and a second branch including a voltage controlled resistance means wherein each of said first and second branches receives a direct current voltage, said bridge circuit further including a first and second output voltage means each connected to a respective one of said first and second branches, each of said transduction cells further including a bridge nulling circuit responsive to an output of said first and second voltage output means to provide a difference voltage, said bridge nulling circuit also including an integrator means for providing a feedback signal;

a summing means in each of said cells for receiving the feedback signal from said each cell and from neighboring ones of said cells in said array and outputting a local control voltage whereby said each cell will have its respective bridge at null and wherein said local control voltage controls its respective voltage controlled resistance means and wherein each respective feedback signal corresponds to a spatially filtered output from each transduction cell in the array, and wherein said summation of said feedback signal varies until the difference between said first and said second output voltage is zero at which point said feedback signal remains constant and is proportional to said sensor resistance as a function of the transfer characteristics of said voltage controlled resistance.

* * * * *